United States Patent
Hein et al.

(10) Patent No.: US 8,945,506 B2
(45) Date of Patent: Feb. 3, 2015

(54) METHOD OF PRODUCING HYDRATED LIME

(76) Inventors: Gregory S. Hein, Katy, TX (US); Sun Yong Kim, Hayward, CA (US)

( * ) Notice: Subject to any disclaimer, the term of this patent is extended or adjusted under 35 U.S.C. 154(b) by 185 days.

(21) Appl. No.: 13/397,769

(22) Filed: Feb. 16, 2012

(65) Prior Publication Data

US 2013/0213264 A1   Aug. 22, 2013

(51) Int. Cl.
*C01F 11/02* (2006.01)
*C01B 13/14* (2006.01)

(52) U.S. Cl.
USPC ............................ 423/640; 423/635; 423/636

(58) Field of Classification Search
None
See application file for complete search history.

(56) References Cited

U.S. PATENT DOCUMENTS

| | | | |
|---|---|---|---|
| 3,131,074 A | 4/1964 | Thompson | |
| 4,208,388 A * | 6/1980 | Nicholson | 423/268 |
| 5,492,685 A | 2/1996 | Moran et al. | |
| 5,525,509 A * | 6/1996 | Christner et al. | 435/265 |
| 2004/0258612 A1 * | 12/2004 | Huege et al. | 423/640 |
| 2008/0216712 A1 | 9/2008 | Bailey | |
| 2008/0273925 A1 | 11/2008 | Borden et al. | |

OTHER PUBLICATIONS

Triton X Series product descriptions from Dow website, accessed Jun. 4, 2014, http://www.dow.com/surfactants/products/octyl.htm.*

* cited by examiner

*Primary Examiner* — Melvin C Mayes
*Assistant Examiner* — Colin W Slifka
(74) *Attorney, Agent, or Firm* — Zarley Law Firm, P.L.C.

(57) ABSTRACT

A method of producing a hydrated lime. The process hydrates quicklime in conjunction with standard means of hydrating lime. The resulting hydrated lime has highly reduced contents of calcium oxide and magnesium oxide. The hydrated lime has little to no remaining reactivity when placed in contact with water after the process. The hydrated lime can is with stoichiometric volumes of water as required to fully hydrate the quicklime and water mixture as well as with volumes beyond the calculated stoichiometry with some potential for remaining water left after the process without the potential for lime putty or a wet hydrate as the result.

20 Claims, 1 Drawing Sheet

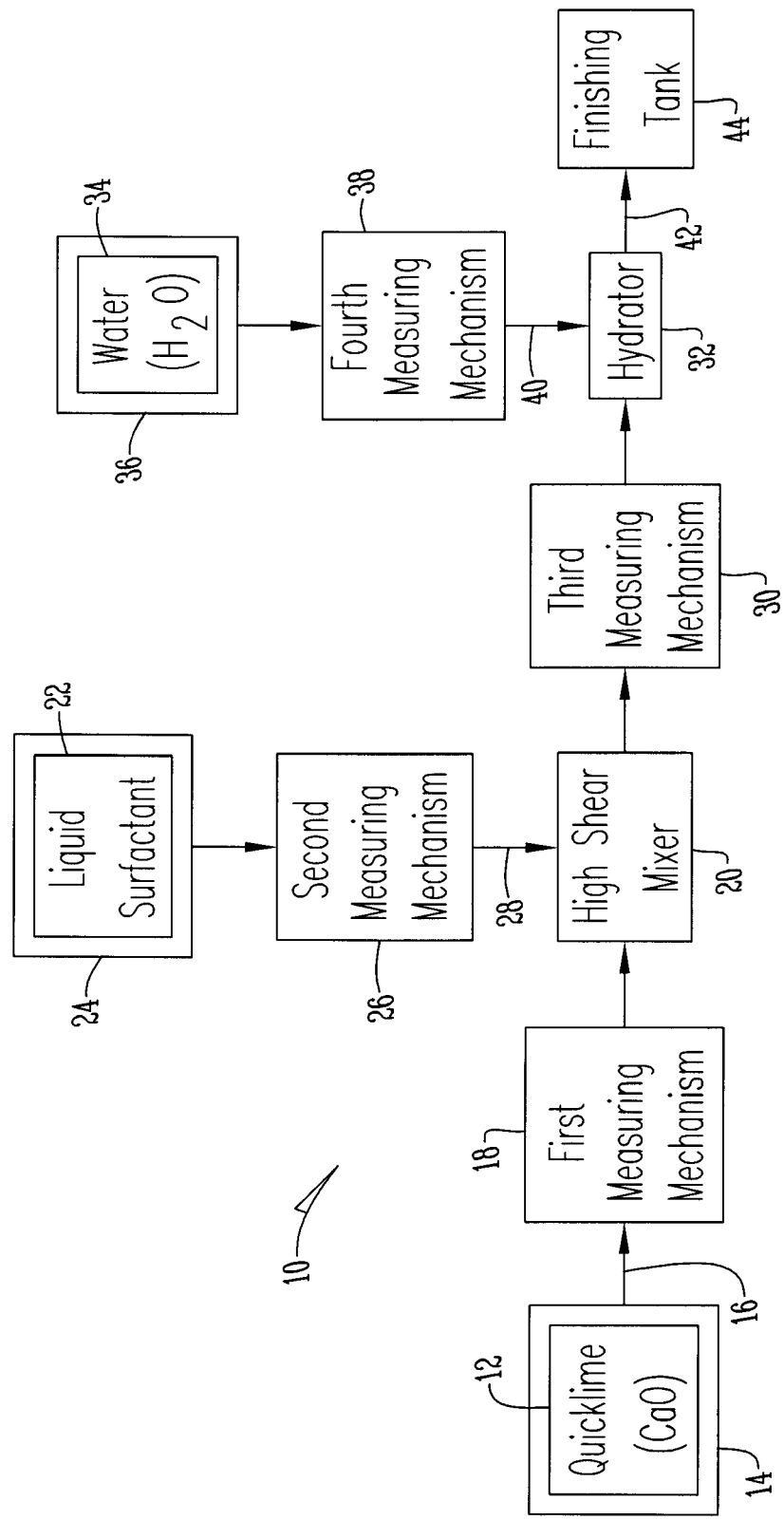

METHOD OF PRODUCING HYDRATED LIME

BACKGROUND OF THE INVENTION

"Lime" is a general term used for calcium-containing inorganic materials, in which carbonates, oxides and hydroxides predominate. Lime is used in large quantities as building and engineering materials (including limestone products, concrete and mortar) and as chemical feedstocks, among other uses. Lime is typically derived from mined limestone or chalk, which are composed primarily of calcium carbonate. These rocks may be crushed or pulverized and chemically altered through various processes. "Burning" (calcination) converts lime into the highly caustic material known as "quicklime" (calcium oxide, CaO). Through subsequent addition of water, quicklime is converted into the less caustic (but still strongly alkaline) slaked lime or hydrated lime (calcium hydroxide, Ca(OH)2). The process of converting quicklime to slaked lime or hydrated lime is called slaking of lime.

The chemical reactions describing the production of high calcium or dolomitic based lime hydrate are as follows:

Hydrate from A High Calcium Lime
$$CaO + H_2O \Longrightarrow Ca(OH)_2 + Heat$$

Hydrate from A Dolomitic Lime (Atmospheric Pressure)
$$CaO \cdot MgO + H_2O \Longrightarrow Ca(OH)2 + MgO + Heat$$

Hydrate from A Dolomitic Lime (Under Pressure)
$$CaO \cdot MgO + 2H_2O \xRightarrow{Pressure} Ca(OH)_2 + Mg(OH)_2 + Heat$$

Quite often the terms Hydrated Lime and Slaking are used interchangeably; however there is a definite and distinct difference between the two terms. Hydrated Lime is defined as a process whereby approximately stoichiometric amounts of water and lime react to form a product, hydrate, which is a dry powder; i.e. it contains less than 1% free moisture and is handled as a powder. In contrast, slaking is defined as a process whereby lime is reacted with an excess amount of water to form a lime slurry which is handled as a liquid. Hydrated lime is a very well-known and understood material that has been used for many years as an additive into many different industrial applications. It is formed when quicklime or calcium oxide (CaO) comes into contact with water. When water is added to quicklime an exothermic reaction takes place which converts the CaO to $Ca(OH)_2$. This exothermic reaction is known to drive off the water the calcium oxide reacts with in a very extreme rise in temperature while releasing evaporated water. Once the material has reacted it becomes very stable and is thereafter used in many applications from civil engineering work, additives in food, to stabilize soils and foundations, and the like.

The quality of raw lime materials vary with the quality of the rock formations from which it is mined. Limestone deposits differ in quality by many aspects. One of the most measurable differences is the magnesium content of the deposit. As magnesium content increases to higher levels, a different grade of lime is the end result. This high magnesium content lime is called "dolomitic lime" and is preferred in the production of certain end products.

The production of hydrated lime starts at a limestone quarry. The limestone, $CaO_3$, is mined as a mineral from the characteristic quarry for the desired final product use. The limestone is processed to a fineness required for the energy intensive kiln process wherein $CO_2$ is driven off and the result is a fine white product comprised mostly of CaO and a percentage of MgO (dependent on the mineral deposit within the quarry). Since the CaO and MgO are very reactive with water, the material is either immediately hydrated on site at a hydration facility or stored in a low moisture environment.

There are many lime hydration facilities throughout the world. Although there are many specific and unique ways to hydrate specific quicklimes, the most common ways involve one of two types of process. The first is a non-pressure environment which is most commonly used for high calcium quicklime where the magnesium oxide content is less than 7%. The second involves high pressure process wherein the higher magnesium oxide content limes (where the magnesium oxide content is more than 7%) are hydrated more fully than without the use of pressure.

The amount of pressure can be modified to aid in the hydration of the MgO, which is harder to hydrate than CaO. In addition, the amount of water that can also be modified to aid in the hydration process. Slaking is often used for the process which involves the use of greater than stoichiometric amounts of water beyond what is needed for the full reaction and results in a liquid-lime slurry.

The improved process is a modification to the dry hydration process.

BRIEF SUMMARY OF THE INVENTION

A method of producing a super hydrated lime (SHL) by either a batch or continuous process as a process incorporated into an existing lime hydration facility or as a stand-alone process. The process hydrates quicklime in conjunction with standard means of hydrating lime within or without a controlled pressure environment. The resulting hydrated lime has highly reduced contents of calcium oxide, magnesium oxide and a carbon chain bonded to the structure giving it qualities much different than hydrated limes manufactured by current production processes. Therefore, as a hydrated lime the final hydrated lime has little to no remaining reactivity when placed in contact with water after the process, as compared to the state of the art, and proves superior for use in many applications for which hydrated lime is used at present and allows for more tolerance for error within the production process. The super hydrated lime is formed through the process of weighing stoichiometric volumes of water as is required to fully hydrate the quicklime. The next steps are placing a surfacant and quicklime in a mixer, mixing the surfacant and quicklime mixture in the mixer, and then adding water to the mixture to form a super hydrated lime.

BRIEF DESCRIPTION OF THE DRAWINGS

The FIGURE is a schematic diagram of a system that performs a method of forming hydrated lime.

DETAILED DESCRIPTION OF THE INVENTION

The super hydrated lime process 10 involves the incorporation of an additional step to the hydrated lime production process that is not presently performed. Upon completion of the formation of quicklime 12, through the quicklime formation process, the quicklime 12 is typically conveyed to a storage silo 14 to await delivery as quicklime 12 to customers or for immediate use in the hydration process. The super hydrated lime process 10 adds a circuit to the standard quicklime hydration process.

The super hydrated lime process 10 is as follows, the quicklime 12 (CaO) leaves the storage silo 14 mechanically, such as through a conveyor 16. The quicklime 12 (CaO) is conveyed to a first measuring mechanism 18 which weighs or measures a known quantity of quicklime 12. This known quantity of quicklime 12 is added to at least one mixer 20. Preferably, depending upon size, the mixer 20 is a high shear mixer that can range anywhere between 5 and 200 rpm.

The process includes a liquid surfactant 22, which is stored in a first storage tank 24. The liquid surfactant 22 is conveyed to a second measuring mechanism 26 which weighs or measures a known quantity of liquid surfactant 22. This known quantity of liquid surfactant 22 is added to the mixer 20 through a first dispensing device 28 that in a preferred embodiment is a set of nozzles.

The surfactant 22 is added in a proportion required by the chemistry of the quicklime 12 to ensure the proper and complete coating of the maximum surface area of the quicklime 12 (CaO) possible. The amount of surfactant 22 added is varied as the grain size of finished quicklime 12 (CaO) varies.

In addition, the manner in which the quicklime 12 and surfactant 22 are added to the mixer 20 is also varied. In one arrangement, the full quantity of quicklime 12 and surfactant 22 are added at the same time and mixed together. In another arrangement the full quantity of the quicklime 12 or surfactant 22 is added to the mixer 20 while the other material is slowly added to the mixer 20 while mixing occurs. In another arrangement the quicklime 12 and surfactant 22 are both added at controlled rates to the mixer 20. In one arrangement quicklime 12 and liquid surfactant 22 are added to the mixer 20 in a continuous flow process, where raw materials are continuously going into the mixer 20 and mixed quicklime 12 and liquid surfactant 22 are continuously flowing out of the mixer 20. In another arrangement, quicklime 12 and liquid surfactant 22 are added to the mixer 20 in a batch process, where raw materials are added in batches to at least one mixer 20 and mixed quicklime 12 and liquid surfactant 22 are removed from the mixer 20.

Mixing continues until the surface area of the quicklime 12 is coated with surfactant. While a standard mixing time can be calculated, mixing time can vary depending on variation in the inputs to the process 10. Mixing time depends upon the grain size of quicklime 12 (CaO), quantity of quicklime 12 (CaO) added, impurities in the quicklime 12, amount of surfactant 22 added, the type of surfactant 22 used, manner in which the quicklime 12 and surfactant 22 are added to the mixer 20, the speed, design or manner of operation of the mixer 20, or any other variation in the process including variation in mixer type that satisfies the aforementioned variables.

Next, the quicklime 12 and surfactant 22 mixture is conveyed to a third measuring mechanism 30. The quicklime 12 and surfactant 22 mixture is then weighed or measured and a specified quantity of the quicklime 12 and surfactant 22 mixture is added to a hydrator 32 for initiation of the hydration reaction. Hydration occurs in the hydrator 32 at atmospheric pressure. Alternatively, pressure is added to or contained within the hydrator 32 such that the hydration occurs at higher than atmospheric pressure.

Water, or another hydrating liquid, 34, is stored in a second storage tank 36. The liquid 34 is conveyed to a fourth measuring mechanism 38 which weighs or measures a known quantity of liquid 34. This known quantity of liquid 34 is added to the hydrator 32 through a second dispensing device 40 that in a preferred embodiment is a set of nozzles.

Water or another hydrating liquid 34 is added to the quicklime 12 and surfactant 22 mixture within the hydrator 32. As water 34 is added, a chemical process occurs within the hydrator 32. The heat of the hydration process bonds the carbon chains of the surfactant 22 and quicklime 12 along with the water 34 creating a modified hydrated lime or super hydrated lime 42. The modified chemistry of this material creates a modified product having similar characteristics when added to water as an oil/water mixture. Where the surface tension between the resulting hydrated lime 42 is very high due to the modification of the surface chemistry. The resulting hydrated lime 42 is fully hydrated to the point that the hydrated lime 42 is 90% to 100% insoluble in water and unmixable with water directly.

A properly administered process will result in a 100% insoluble and hydrophobic powder. A process whereby residence times or volumes of additives are not specifically adhered to nets a 90% insoluble hydrophobic powder.

In some arrangements, depending on certain variables in the process 10, resulting hydrated lime 42 is conveyed to a finishing tank 44. Finishing tank is any containment or storage device with mixing that will allow for the final finished product, the hydrated lime 42, to be completely hydrated and therefore allow for the completion of the reaction. The finishing tank 44 may be required in certain existing lime hydration facilities if the existing hydrator 32 does not allowing for the proper time to hydrate the super hydrated lime 42 completely.

The liquid surfactant 22 can be a blend of one or more oils that do not mix with water. Both stability requirements and economics govern the best or optimal blend of surfactant oils to be required for specific applications. Specifically, the following types of surfactants work in this process: alcohols, preferably ethanol or methanol in conjunction with small proportions of detergents with dimethyl siloxane used as an antifoaming agent within the surfactant blend.

It is also possible to blend various cationic and anionic enzymes at varying percentages to modify the chemistry for specific applications as required for the final end product. Surfactants preferably do not contain any percentages of water.

Thus the hydrated lime 42 consists of by volume 0.5-40% (% of total water) surfactant (surface modifier agent mixture) of which 50%-99.5% by volume is oils, including petroleum or non-petroleum oils, new or recycled, 0.5%-50% by volume as catalyst/enzymes and surfactants and detergent regarded for the specified hydration a varies with the surfactant. A water additive in one embodiment is added in multiple steps for both hydration control and quality control of the hydrated lime process. Alternatively a water soluable dimethyl siloxane as an additional coating agent or performance enhancer can be added as desired within the product.

The additional step involved in this process can be incorporated directly into an existing lime hydration facility or can be situated at an offsite production facility. This ultimately depends on the economic benefit derived from the process. Quick lime 12 (CaO) has a much higher density (approximately 60 pcf) than does super hydrated lime 42 which has a density of (approximately 30 pcf), so transportation economics can govern which model is better for the placement of a facility.

What is claimed is:
1. A method of forming super hydrated lime comprising the steps of:
 adding a quantity of quicklime to a mixer;
 adding a quantity of surfactant that contains no water to the mixer;
 mixing the quicklime and surfactant in the mixer until the surface area of the quicklime is coated with surfactant to form a mixture that contains no water;

adding a quantity of water to the mixture to bond the surfactant to the quicklime to form a super hydrated lime material.

2. The method of claim 1 further comprising the step of mixing the hydrated lime material to ensure proper hydration.

3. The method of claim 1 further comprising the step of adding the quicklime and the surfactant to the mixer in a batch process.

4. The method of claim 1 further comprising the step of adding the quicklime and the surfactant to the mixer in a continuous process.

5. The method of claim 1 further comprising the step of adding the mixture and the water in a hydrator.

6. The method of claim 1 further comprising the step of conveying the hydrated lime material to a finishing tank to ensure full hydration.

7. The method of claim 1 further comprising the step of measuring the quantity of quicklime and surfactant in proportion to one another for complete coating of the quicklime by the surfactant.

8. The method of claim 1 wherein hydration of the mixture occurs at atmospheric pressure within a hydrator.

9. The method of claim 1 wherein hydration of the mixture occurs above atmospheric pressure within a hydrator.

10. The method of claim 1 wherein water is added at an amount no greater than needed for full reaction of the mixture.

11. The method of claim 1 wherein water is added at an amount more than the amount needed for full reaction of the mixture.

12. The method of claim 1 wherein water is added in multiple steps.

13. The method of claim 1 wherein the hydrated lime is produced using high calcium quicklime.

14. The method of claim 1 wherein the hydrated lime is produced using high dolomitic quicklime.

15. The method of claim 1 further comprising the step of adding a quantity of enzymes to the mixer.

16. The method of claim 15 wherein the enzyme consists of the group including cationic and anionic enzyme.

17. The method of claim 1 further comprising the step of adding a quantity of a water soluble dimethyl siloxane to the mixer as a coating agent.

18. The method of claim 1 wherein the surfactant includes a detergent.

19. The method of claim 1 wherein the surfactant includes an antifoaming agent.

20. A method of forming super hydrated lime comprising the steps of:
conveying quicklime to a first measuring mechanism;
measuring a known quantity of quicklime;
adding the measured quicklime to a mixer;
conveying a liquid surfactant that contains no water and having an enzyme from a first storage tank to a second measuring mechanism;
measuring a known quantity of liquid surfactant;
adding the measured liquid surfactant to the mixer through a dispensing device;
mixing the quicklime and liquid surfactant in the mixer until the surface area of the quicklime is coated with liquid surfactant to form a mixture that contains no water;
conveying the mixture to a third measuring mechanism;
measuring a known quantity of the mixture;
adding the measured mixture to a hydrator;
conveying a hydrating liquid from a second storage tank to a fourth measuring mechanism;
measuring a known quantity of hydrating liquid;
adding the measured hydrated liquid to the hydrator through a dispensing device; and
hydrating the mixture within the hydrator to bond the liquid surfactant and quicklime to create a super hydrated lime;
wherein the super hydrated lime is a hydrophobic powder.

* * * * *